(12) United States Patent
Juan et al.

(10) Patent No.: US 9,261,484 B1
(45) Date of Patent: Feb. 16, 2016

(54) ACOUSTIC WAVEGUIDE FOR THE DETECTION AND CHARACTERIZATION OF OBSTRUCTIONS IN LIQUID-FILLED TUBES

(71) Applicant: University of Puerto Rico, San Juan, PR (US)

(72) Inventors: Eduardo J Juan, Cabo Rojo, PR (US); Ricardo H Castaneyra, Mayaguez, PR (US)

(73) Assignee: University of Puerto Rico, San Juan, PR (US)

( * ) Notice: Subject to any disclaimer, the term of this patent is extended or adjusted under 35 U.S.C. 154(b) by 579 days.

(21) Appl. No.: 13/623,069

(22) Filed: Sep. 19, 2012

Related U.S. Application Data

(60) Provisional application No. 61/536,069, filed on Sep. 19, 2011.

(51) Int. Cl.
*G01N 29/28* (2006.01)
*G01N 29/028* (2006.01)

(52) U.S. Cl.
CPC .................................. *G01N 29/028* (2013.01)

(58) Field of Classification Search
CPC ............ G01N 29/028; G01N 29/2462; G01N 29/2468; G01N 29/28
USPC ............ 73/622, 623, 597, 598, 646, 617, 644
See application file for complete search history.

(56) References Cited

U.S. PATENT DOCUMENTS

| 3,420,097 | A | * | 1/1969 | Battermann et al. ............ 73/644 |
| 3,431,440 | A | * | 3/1969 | Osgood .......................... 73/644 |
| 3,555,891 | A | * | 1/1971 | Lewis ............................. 73/644 |
| 4,033,178 | A | * | 7/1977 | Holt et al. ....................... 73/644 |
| 4,428,379 | A | * | 1/1984 | Robbins et al. ............... 600/461 |
| 2012/0060591 | A1 | * | 3/2012 | Faustmann et al. .......... 73/64.53 |

FOREIGN PATENT DOCUMENTS

WO   WO 2010/136350 A1 * 12/2010 ............. G01N 29/22

* cited by examiner

*Primary Examiner* — Laura Martin
*Assistant Examiner* — Rose M Miller
(74) *Attorney, Agent, or Firm* — Hoglund & Pamias, PSC; Roberto J. Rios

(57) ABSTRACT

The present invention provides an acoustic waveguide for determining and continuously monitoring the degree, location and type of obstructions in liquid-filled tubes or catheters using acoustic waves. The tube's wall has an intermediate layer positioned between a tube outer wall and a tube inner wall of the tubea and the intermediate layer is made of a material having a difference in acoustic impedance of at least one order of magnitude with respect to that of the liquid present in or outside the waveguide reducing or eliminating the amount of acoustic energy that radiates through the tube.

11 Claims, 5 Drawing Sheets

US 9,261,484 B1

ACOUSTIC WAVEGUIDE FOR THE DETECTION AND CHARACTERIZATION OF OBSTRUCTIONS IN LIQUID-FILLED TUBES

GOVERNMENT INTEREST

The claimed invention was made with U.S. Government support under grant number 5S06GM008103 awarded by the National Institute of Health (NIH). The government has certain rights in this invention.

FIELD OF THE INVENTION

The present invention relates to an apparatus for determining and continuously monitoring the degree, location and type of obstructions in liquid-filled tubes or catheters using acoustic waves.

BACKGROUND OF THE INVENTION

There are several, methods available to inspect the interior of tubes for detecting any obstruction inside. One of these methods relies on acoustic detection for detecting the presence of a blockage in a pipe. In essence, an acoustic transmitter is used to generate an acoustic signal that propagates through the liquid-filled pipe and a transmitter that receives the signal and/or any signal reflection. Data processing means are provided for analyzing and interpreting the signal to determine if a blockage exists in the pipe and its size and location inside the tube. However, there is a constant problem associated with this technology in terms of acoustic signal reflection since tubes or pipes might have different sizes, materials and are subjected to conditions creating a situation where some of the acoustic signal radiates through the tube affecting the analysis and interpretation of the received signal.

Thus, what is needed is a cost-effective tube arrangement that reduces or eliminates the amount of acoustic energy that radiates through the tube.

SUMMARY OF THE INVENTION

According to an aspect of the invention, an acoustic waveguide is provided for determining and continuously monitoring the degree, location and type of obstructions in liquid-filled tubes or catheters using acoustic waves.

According to another aspect of the invention, a tube wall has an intermediate layer between a tube outer wall and a tube inner wall.

According to still another aspect of the invention, the intermediate layer has a material having a difference in acoustic impedance of at least one order of magnitude with respect to that of the liquid present in or outside the waveguide.

BRIEF SUMMARY OF THE INVENTION

Further features and advantages of the invention will become apparent from the following detailed description taken in conjunction with the accompanying figures showing illustrative embodiments of the invention, in which.

DETAILED DESCRIPTION OF THE INVENTION

The present invention described the integration of three main components: a) an acoustic waveguide whose wall has an intermediate layer of a material having an acoustic impedance significantly different than the medium inside the tube, b) single or multiple acoustic transducers used to generate and record acoustic signals and c) a series of algorithms used to interpret acoustic reflections and estimate the location, degree and type of lumen obstructions.

Figure 1:
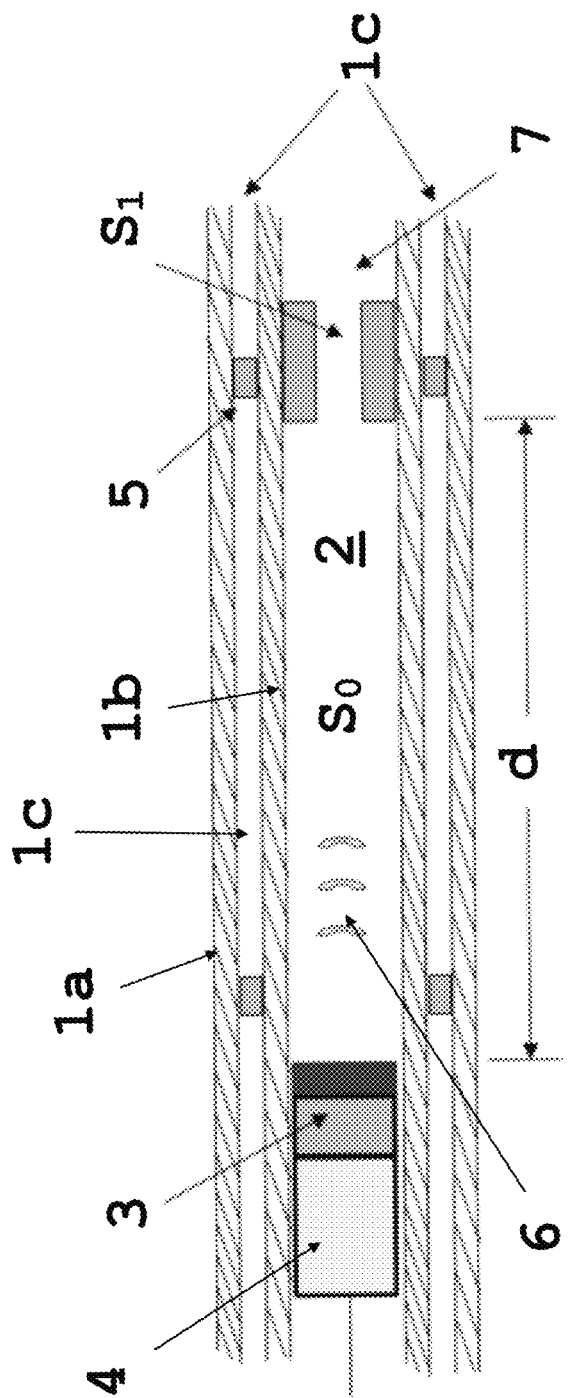
FIG. 1 illustrates an acoustic waveguide according to an embodiment of the present of the invention.
Figure 2:
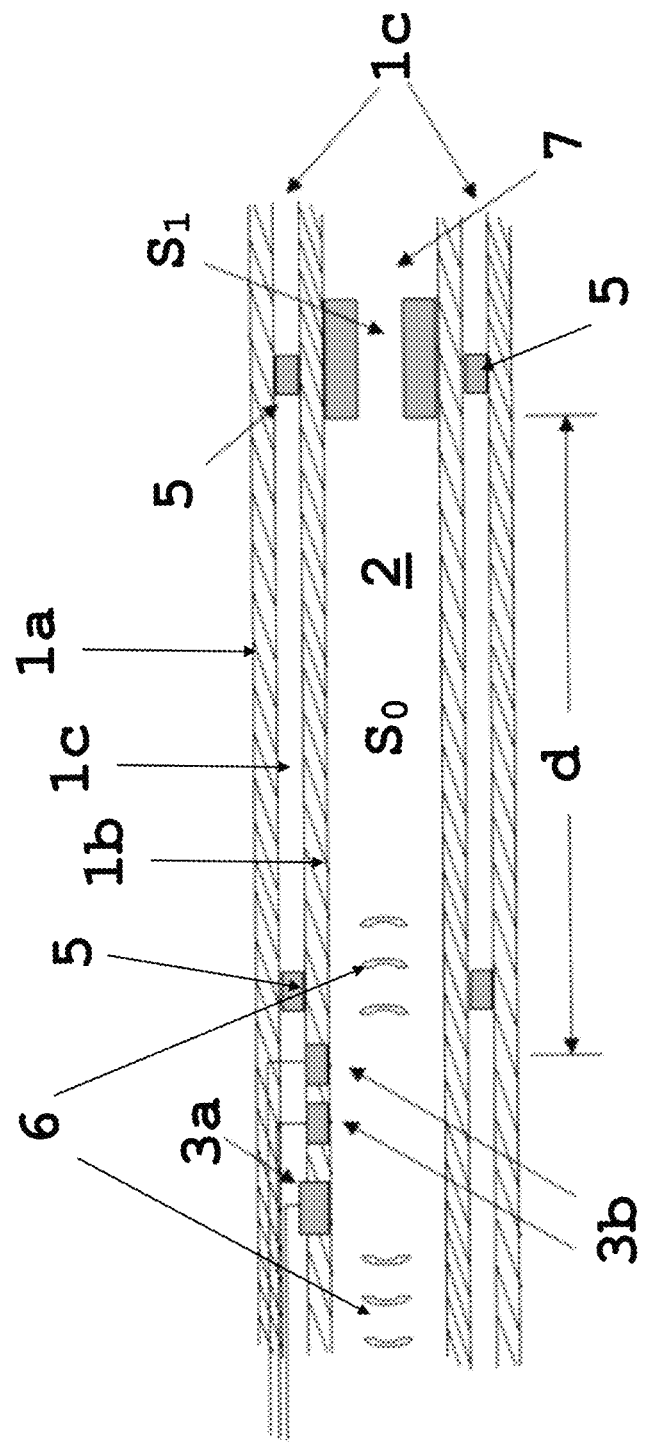
FIG. 2 illustrates an acoustic waveguide according to another embodiment of the present of the invention.

FIG. 1 and FIG. 2 describes two of the preferred embodiments of the invention. The acoustic wave arrangement will be connected to an external monitor or any applicable hardware interface that is used for driving the acoustic transducers, signal processing and analysis, display and use interface as is well known in the art.

FIG. 1 shows an acoustic transducer 3 mounted at the tip an acoustic probe 4. The probe is then inserted into liquid-filled tube 2 of cross-sectional area $S_0$. Acoustic waves 6 are generated by at least one of the transducers, and propagate along the liquid in the tube. Acoustic reflections will, occur whenever there is a change in acoustic impedance. Acoustic impedance changes occur due to changes in several variables, among them changes in composition or geometry of the tube wall or of the propagating medium. If both the tube and the medium are constant throughout the length of the tube, reflections will only occur due to obstructions 7 in the tube's lumen. The resulting reflections are then recorded by the acoustic transducers, and processed and analyzed to determine the location, distance d, and severity, cross-sectional area $S_1$, of lumen obstructions.

In the embodiment depicted in FIG. 2, the acoustic transducers (or single transducer) 3a are embedded in the wall 1b of the liquid-filled tube, such that their active surfaces are flush with the inner wall of the tube. As with the embodiment of FIG. 1, acoustic waves are generated by at least one acoustic transducer 3a and subsequently recorded by at least one receiving acoustic transducer 3b. One advantage of this configuration is that the tube's patency can be monitored without obstructing the tube with an acoustic probe or with the acoustic transducers.

In practice the acoustic waveguide shown in FIG. 1 and FIG. 2, can be any kind of liquid-carrying conduit such as, but not limited to, oil pipelines, hydraulic hoses, plumbing pipes and medical catheters. Although most of these conduits have a circular cross-sectional area, this invention can be used on other cross-sectional geometries (i.e. square or oval) and on waveguides with curves (the tube does not have to be straight). Utilizing acoustic pulse reflectometry in liquid-filled tubes (ie. medical catheters) is a more challenging proposition than using it on air-filled tubes where there are already a number of applications, for various reasons. One reason is that for immersed liquid-filled tubes, when the tube wall material has acoustic impedance that is similar to that of the medium inside and outside of the tube, some of the acoustic energy radiates through the wall as guided waves cannot be fully sustained for all modes. One critical aspect of the invention is that the tube wall has an intermediate layer 1c between a tube outer wall 1a and a tube inner wall 1b of a material having a difference in acoustic impedance of at least one order of magnitude with respect to that of the liquid present in or outside the waveguide. A support element 5 is provided to separate the outer and inner walls 1a, 1b and to provide structural support. This intermediate layer is provided to prevent the radiation of acoustic energy towards the exterior of the tube, thus addressing one of the challenges associated to the use of acoustic reflectometry in liquid-filled tubes. The difference in acoustic impedance of at least one order of magnitude between the intermediate layer of material with respect to that of the liquid inside or outside the waveguide can be explained by the definition of the acoustic reflection coefficient.

The pressure reflection coefficient, defined as the ratio of reflected $p_r(x_0,t)$ to incident $p_i(x_0,t)$ acoustic pressures at a boundary $x_0$ between two layers, is given by $$R(x_0) = \frac{p_r(x_0, t)}{p_i(x_0, t)} = \frac{Z_1 - Z_0}{Z_1 + Z_0}$$

where $Z_0$ and $Z_1$ are the acoustic impedances of the first and second media, respectively. If the value of $Z_1$ is one order of magnitude larger than that of $Z_0$, the resulting pressure reflection coefficient is 0.82. A pressure reflection coefficient of −0.82 would be obtained if the value of $Z_1$ were one order of magnitude smaller than that of $Z_0$. These values of reflection coefficients would result in power transmission and reflection coefficients of 0.33 and 0.67, respectively, indicating that for this case approximately 33% of the acoustic energy would be lost to the outside of the waveguide. For most practical applications, the intermediate layer will consist of a gas, to ensure a large difference in acoustic impedance. As an example, let us consider a water-filled waveguide and an air-filled intermediate layer. The acoustic impedance of water $1.48*10^6$ rayls, while that of air is 415 rayls. In this case, the power transmission coefficient is almost zero, indicating that almost all of the acoustic energy will remain in the waveguide.

In a preferred embodiment, the acoustic transducers 3, 3a, 3b used in both embodiments are made of lead zirconate titanate (PZT) in conjunction with suitable matching and backing layers, using standard procedures described in the scientific literature.

The other challenge of utilizing acoustic reflectometry in liquid-filled tubes is that, in such tubes, multiple acoustic modes can propagate simultaneously, and at different velocities and attenuation rates, causing distortion of the incident wave and therefore making analysis of reflections more difficult. To address this challenge, we have adapted and developed specialized algorithms used to interpret the recorded acoustic reflections and to estimate the size, type and location of lumen obstructions.

Figure 3:
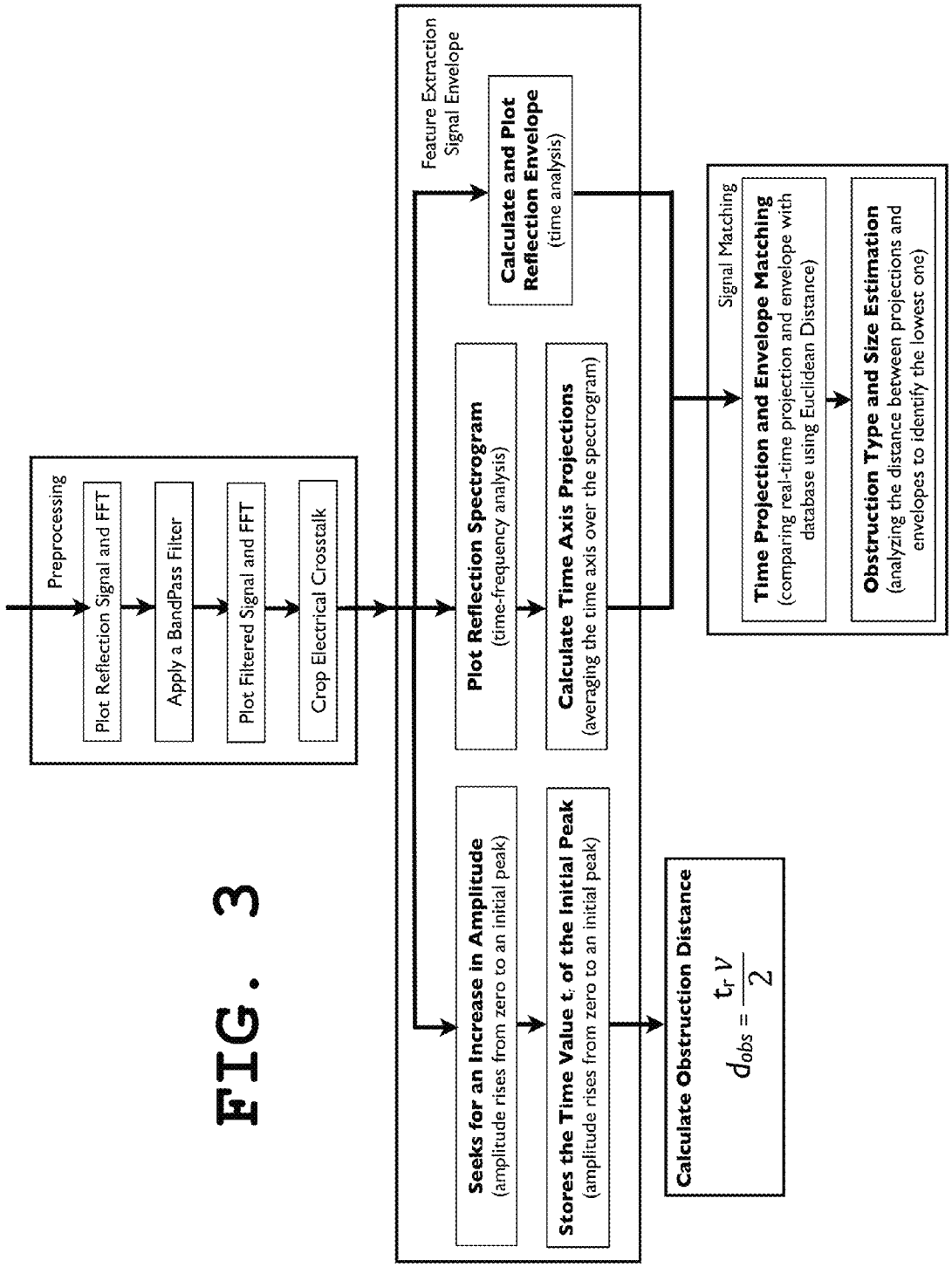
FIG. 3 shows a flowchart for the general procedure of the algorithm to process, analyze and classify acoustic reflections in water-filled tubes according to the present invention.

FIG. 3 presents the general procedure of the algorithm to process, analyze and classify acoustic reflections in water-filled tubes. This type of framework is used in audio identification, where the fundamental processes are signal feature extraction and signal matching. The signal feature extraction derives a set of acoustic signal characteristics. Given a signal feature derived from an acoustic reflection, the signal matching algorithm will search a database of signal features to find the best match. The steps of the overall procedure are described below.

The acoustic reflection preprocessing consists first in reading the reflection data from a text file. Then, a BandPass filter and amplifier is used to reduce low-frequency noise and amplify the acoustic reflection signal, respectively. The acoustic reflection analysis consists of extracting different features that identify a particular signal. The most common transformation used in audio identification is the Fast Fourier Transform. It has been published that the Discrete Fourier Transform is generally less sensitive to time shifting. The main idea of linear transforms is to convert a set of measurements to a new set of features that are stored in a database. To extract different features from the acoustic reflection, two algorithms are used. First is the onset algorithm, which seeks the time when the first increase in amplitude occurs in the reflection time signal. With this estimated time, the distance of the obstruction that produced the reflection is calculated. The other two features that are extracted from the acoustic reflection are its envelope and projection of the spectrogram time axis.

Figure 4:
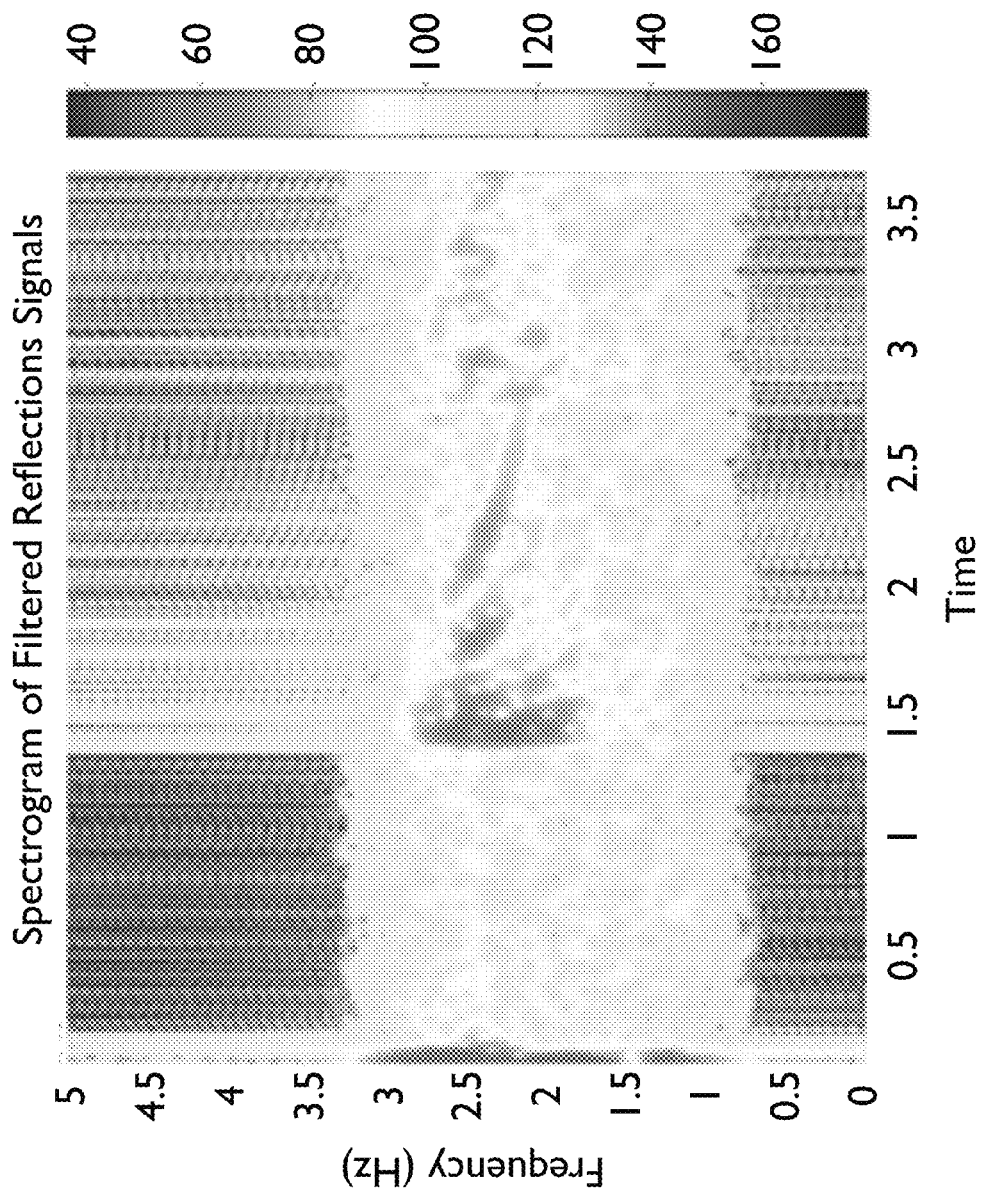
FIG. 4 shows an example spectrogram according to the present invention.

Spectrograms like the one shown in FIG. 4 are images that show how the power spectrum density (PSD) of a signal changes as time elapse. Since spectrograms are images, these can be represented as a m-by-n matrix A, $$A = \begin{matrix} a_{1,1} & a_{1,2} & a_{1,n} \\ a_{2,1} & a_{2,2} & a_{2,n} \\ \vdots & \vdots & \vdots \\ a_{m,1} & a_{m,2} & a_{m,n} \end{matrix},$$

Figure 5:
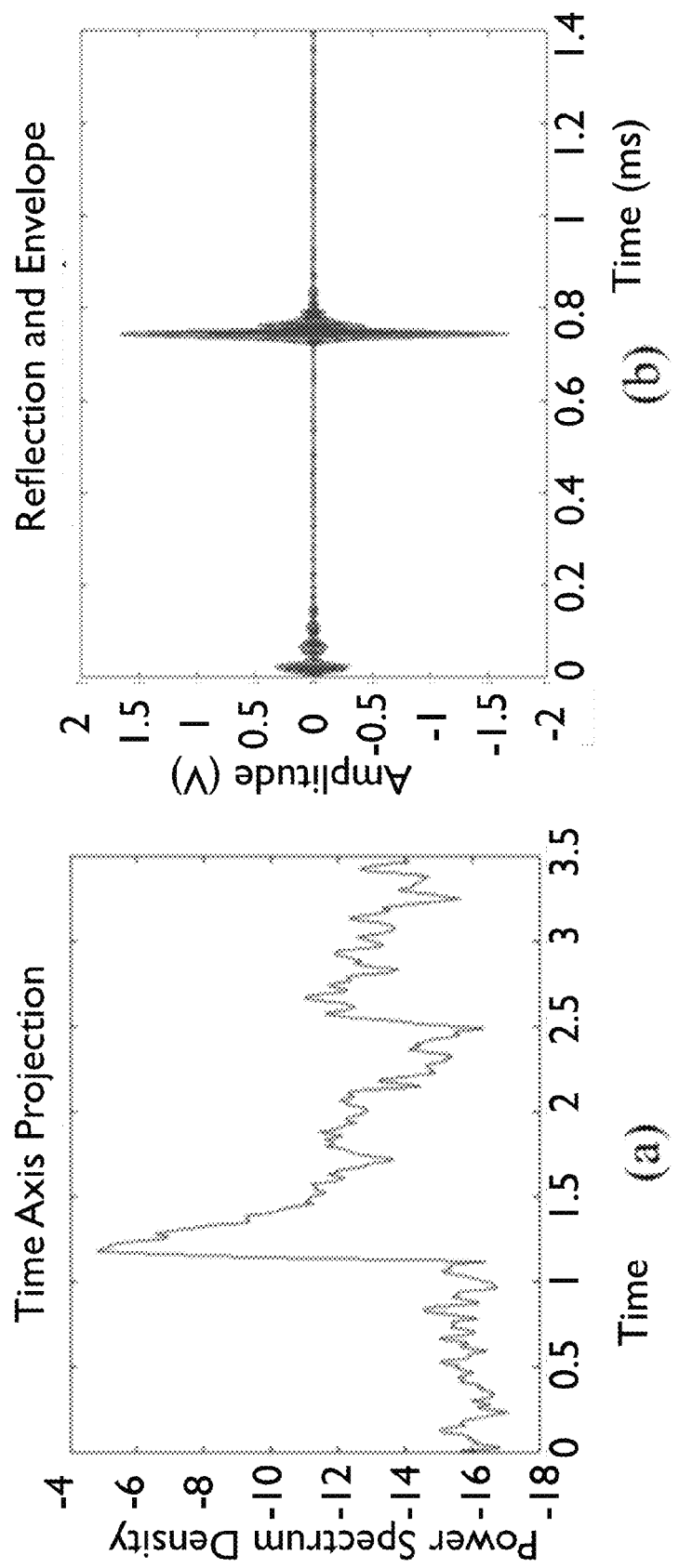
FIG. 5 shows an example of an spectrogram time axis projection and the envelope of an acoustic reflection according to the present invention.

, where m (rows) are discrete frequency values, n (columns) are discrete time values and $a_{m,n}$ is the PSD value at m×n. These discrete values are established by the parameters used in the spectrogram. The time axis can be projected by calculating the average value, maximum value, etc., along the columns of matrix A. FIG. 5 illustrates an example of an spectrogram time axis projection and the envelope of a acoustic reflection.

The feature database is created by preprocessing an acoustic reflection signal and extracting the mentioned features. The acoustic reflections consist of different obstruction types and sizes located at particular positions along the water-filled tube. This results in a reflection database that contains features for different obstruction types and sizes at specific locations in the water-filled tube.

The procedure used to create the database is also used to process unknown acoustic reflections. Once unknown signals are processed, these are compared with the database using a signal-matching algorithm. Acoustic signature matching is commonly calculated using a distance measure between feature vectors rather than a direct binary match. Some distance metrics methods used in audio matching are the Euclidean distance and the Nearest Neighbor, Manhattan distance and another error metric called Exponential Pseudo Norm. While distances are calculated, these are accumulated to decide if there is a correct identification, seeking the lowest distance. This results in an estimation of the type, size and position of the obstruction.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:

1. An acoustic waveguide comprising:
   a pipe filled with a liquid having an outer wall and a separate inner wall concentric and coaxial with said outer wall; a dividing support positioned between said outer wall and said separate inner wall; an intermediate layer positioned between said outer wall and said inner wall effectively separating said outer wall from said inner wall, wherein said intermediate layer comprises a material having a difference in acoustic impedance of at least one order of magnitude with respect to that of the liquid present in the pipe.

2. The acoustic waveguide of claim 1, wherein said material has a difference in acoustic impedance of at least one order of magnitude with respect to that of a liquid outside the pipe.

3. The acoustic waveguide of claim 1, wherein said material comprises a gas.

4. The acoustic waveguide of claim 3, wherein said gas comprises air.

5. The acoustic waveguide of claim 1, further comprising an acoustic transducer generating an acoustic signal.

6. The acoustic waveguide of claim 5, further comprising an acoustic receiver receiving the reflections of said acoustic signal.

7. The acoustic waveguide of claim 6, wherein said acoustic transducer and said acoustic receiver are integrally formed.

8. The acoustic waveguide of claim 6, wherein said acoustic receiver comprises a plurality of acoustic receivers.

9. The acoustic waveguide of claim 6, wherein said acoustic transducer and said acoustic receiver are integrally formed within said inner wall and mounted flush facing the interior portion of said pipe.

10. The acoustic waveguide of claim 1, wherein said difference in acoustic impedance of at least one order of magnitude greater with respect to that of the liquid present in the pipe.

11. The acoustic waveguide of claim 1, wherein said difference in acoustic impedance of at least one order of magnitude lower with respect to that of the liquid present in the pipe.

* * * * *